United States Patent [19]

Scherowsky et al.

[11] Patent Number: 5,310,499

[45] Date of Patent: May 10, 1994

[54] OXAZOLIDINONE DERIVATIVES, AND THE USE THEREOF AS DOPES IN LIQUID-CRYSTAL MIXTURES

[75] Inventors: Günter Scherowsky; Michael Sefkow, both of Berlin; Gerd Illian, Frankfurt am Main; Rainer Wingen, Hattersheim am Main, all of Fed. Rep. of Germany

[73] Assignee: Hoechst Aktiengesellschaft, Frankfurt am Main, Fed. Rep. of Germany

[21] Appl. No.: 732,626

[22] Filed: Jul. 19, 1991

[30] Foreign Application Priority Data

Jul. 21, 1990 [DE] Fed. Rep. of Germany ....... 4023216
Jul. 24, 1990 [DE] Fed. Rep. of Germany ....... 4023493

[51] Int. Cl.$^5$ ................... C09K 19/34; C07P 263/04; C07D 239/02
[52] U.S. Cl. ............................. 252/299.61; 544/296; 544/315; 544/335; 548/225; 548/229
[58] Field of Search ...................... 252/299.01, 299.61; 544/238, 295, 296, 300, 315, 335, 336, 357, 359, 360, 374, 392; 546/1, 255, 256, 257, 275, 283; 548/225, 226, 229, 227, 230

[56] References Cited

U.S. PATENT DOCUMENTS

| | | | |
|---|---|---|---|
| 5,124,069 | 6/1992 | Nakauchi et al. | 252/299.61 |
| 5,149,462 | 9/1992 | Sakashita et al. | 252/299.61 |
| 5,151,214 | 9/1992 | Koden et al. | 252/299.61 |
| 5,164,113 | 11/1992 | Ikemoto et al. | 252/299.61 |
| 5,215,678 | 6/1993 | Koden et al. | 252/299.61 |

FOREIGN PATENT DOCUMENTS 306919 3/1989 European Pat. Off. .
361272 4/1990 European Pat. Off. .

Primary Examiner—Philip Tucker
Attorney, Agent, or Firm—Curtis, Morris & Safford

[57] ABSTRACT

Chiral oxazolidinones of the formula (I) or (II)

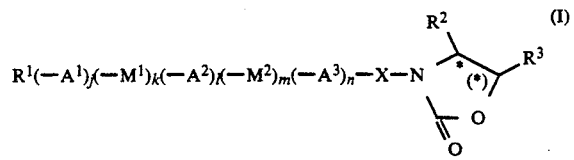

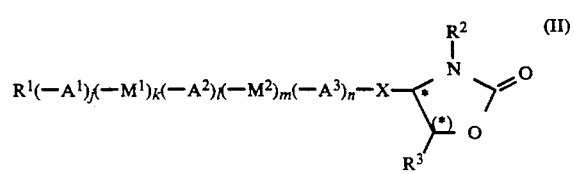

in which
$R^1$ is, for example, a straight-chain or branched alkyl radical having 1 to 16 carbon atoms or
$R^2$ and $R^3$ are, for example, —H, —CH$_3$ or phenyl,
j, l and n are zero, 1 or 2,
k and m are zero or 1,
$A^1$, $A^2$ and $A^3$ are, for example, phenyl or cyclohexyl,
$M^1$ and $M^2$ are, for example, COO or CH$_2$O, and
X is, for example, CH$_2$ or COO, are suitable as dopes in liquid-crystal mixtures. They result in liquid-crystalline ferroelectric phases having short response times. A further advantage is that the oxazolidinones induce a helix of very low pitch, so that they are also suitable for helix compensation in LC mixtures.

5 Claims, No Drawings

OXAZOLIDINONE DERIVATIVES, AND THE USE THEREOF AS DOPES IN LIQUID-CRYSTAL MIXTURES

Particularly in the last decade, liquid crystals have been introduced into various technical areas in which electrooptical and display-device properties are required (for example in watch, calculator and typewriter displays). These display devices depend on dielectric alignment effects in the nematic, cholesteric and/or smectic phases of the liquid-crystalline compounds, the longitudinal molecular axis of the compounds adopting—as a consequence of the dielectric anisotropy—a preferred alignment in an applied electrical field. The customary response times in these display devices are too long for many other potential areas of application of liquid crystals. This disadvantage becomes particularly noticeable if it is necessary to address a large number of pixels. The costs for the production of equipment containing relatively large screen areas, such as, for example, of video equipment, are then generally too high.

In addition to nematic and cholesteric liquid-crystals, optically active smectic liquid-crystal phases have also increased in importance over the last few years.

Clark and Lagerwall were able to show that the use of ferroelectric liquid-crystal systems in very thin cells gives optoelectrical switching or display devices which, compared with conventional TN ("twisted nematic") cells, have response times which are faster by a factor of up to 1000 (cf., for example, Lagerwall et al., "Ferroelectric Liquid Crystals for Displays", SID Symposium, October Meeting 1985, San Diego, Calif., USA). On the basis of these and other favorable properties, for example the possibility for bistable switching and the contrast which is virtually independent of the viewing angle, FLCs are in principle highly suitable for the abovementioned areas of application, for example via matrix addressing.

Electrooptical switching and display elements require either compounds which form tilted or orthogonal smectic phases and are themselves optically active, or compounds which, although forming smectic phases of this type, are not themselves optically active, but can be doped with optically active compounds to induce ferroelectric smectic phases. The desired phase should then be stable over the broadest possible temperature range.

In order to achieve good contrast conditions in electrooptical components, a uniform planar alignment of the liquid crystals is necessary. Good alignment in the $S_A^*$ and $S_C^*$ phase can be achieved if the phase sequence of the liquid-crystal mixture with decreasing temperature is as follows:

$$Isotropic \rightarrow N^* \rightarrow S_A^* \rightarrow S_C^*$$

It is a prerequisite that the pitch of the helix in the $N^*$ phase is very high (greater than 10 μm) or even better is fully compensated (see, for example, T. Matsumoto et al., pp. 468–470, Proc. of the 6th Int. Display Research Conf., Japan Display, Sept. 30–Oct. 2, 1986, Tokyo, Japan; M. Murakami et al., ibid., pp. 344–347). This is achieved by adding to the chiral liquid-crystal mixture which has, for example, a left-hand helix in the $N^*$ phase a further optically active dope which induces a right-hand helix in such amounts that the helix is exactly compensated.

It has now been found that optically active oxazolidinones as dopes in tilted smectic liquid-crystal phases result in a considerable twist in the cholesteric phase even when admixed in small amounts.

This helix induced in the $N^*$ phase can advantageously be used in mixtures for selective compensation of the pitch. It is particularly advantageous here that the dopes according to the invention, as a consequence of their high twist capacity, compensate the pitch of another dope even when added in small amounts.

The invention therefore relates to the use of chiral or optically active oxazolidinones as dopes in liquid-crystal mixtures. The invention furthermore relates to liquid-crystal systems which contain chiral or optically active oxazolidinones, and to novel chiral oxazolidinones (both as optically active compounds and as racemic mixtures). The oxazolidinones to be employed according to the invention conform to the formula (I) or (II)

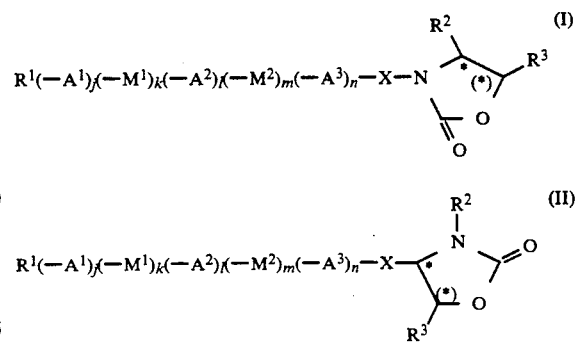

in which
* is a chiral center,
(*) is an optional chiral center,
$R^1$ is a straight-chain or branched alkyl radical having 1 to 16 carbon atoms or a straight-chain or branched alkenyl radical having 3 to 16 carbon atoms, it being possible for these radicals to themselves contain asymmetrical carbon atoms, it being possible for one or more nonadjacent —CH$_2$— groups to be replaced by —O—, —S—, —CO—, —O—CO—and/or —CO—O—, and it being possible for one or more H atoms to be replaced by F, Cl, Br or CN,
—$R^2$ and —$R^3$, independently of one another, are —H, alkyl having 1 to 12 carbon atoms, in which one —CH$_2$—group may also be replaced by —O— or —S—and in which the terminal CH$_3$ group may also be replaced by CH$_2$OR$^4$, CH$_2$SR$^4$, CH$_2$COOR$^4$ or CH$_2$CONH$_2$ where R$^4$ is alkyl having 1 to 10 carbon atoms, or are -phenyl or -cyclohexyl, which may also be substituted by —OR$^4$, —F or —I; .
(—$R^2$ and —$R^3$ are preferably —H, —CH$_3$,

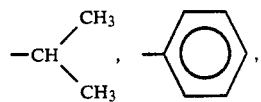

-continued

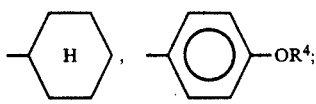

j and l are zero, 1 or 2,
k and m are zero or 1, and
n is zero, 1 or 2,
with the proviso that k is zero if j and/or l are zero; m is zero if n is zero; the sum of j+l+n is at least 1 and at most 3,
—$A^1$ and —$A^2$ are

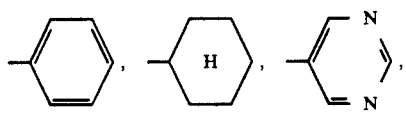

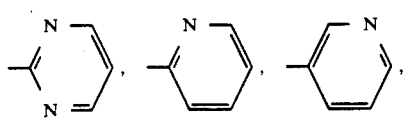

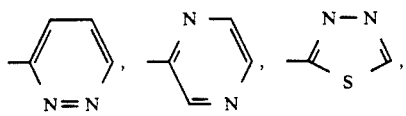

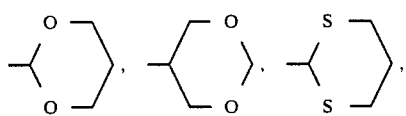

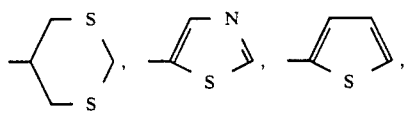

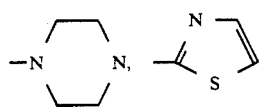

—$A^3$ is

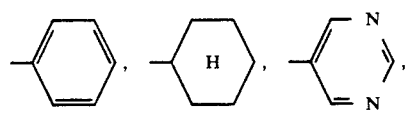

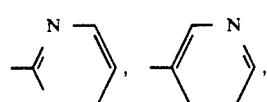

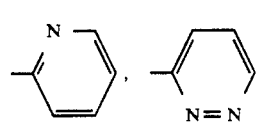

—$M^1$ and —$M^2$ are —CO—O, —O—CO, —CH$_2$CH$_2$, —CH=CH, —CH$_2$O or —OCH$_2$, and
—X— is —O—CH$_2$, —CH$_2$—,

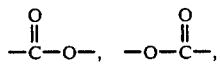

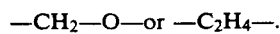

—CH$_2$—O— or —C$_2$H$_4$—.

In a preferred embodiment, the symbols in the formula (I) have the following meanings:

$R^1$ is a straight-chain or branched alkyl or alkenyl radical which has 4 to 14 carbon atoms and may contain an asymmetrical carbon atom or in which one —CH$_2$—group may be replaced by —O—, —CO—or —CO—O—or in which one or more H atoms may be replaced by F, and j, k, l and m are zero or 1.

A further preferred embodiment uses oxazolidinones of the formula (I) in which $R^1$ is a straight-chain or branched alkyl or alkenyl radical which has 6 to 12 carbon atoms and may contain an asymmetrical carbon atom and in which one CH$_2$ group may be replaced by —O—, —CO—or —COO—, and the group (—$A^1$)-(—$M^1$)$_k$(—$A^2$)$_l$(—$M^2$)$_m$(—$A^3$)$_n$—has the following meaning:

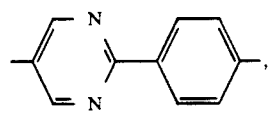

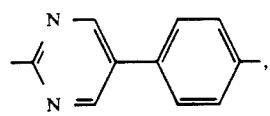

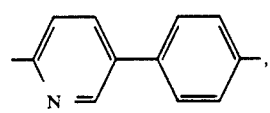

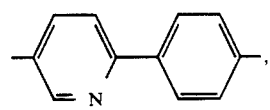

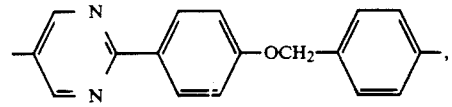

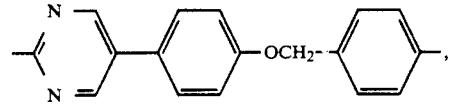

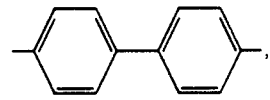

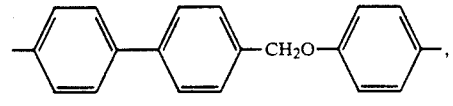

-continued

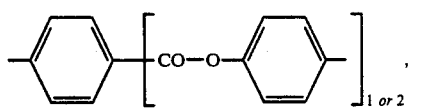

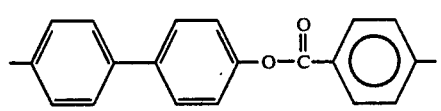

Likewise preferred are oxazolidinones of the formula (I) or (II) in which M is COO, OCO, CH$_2$O or OCH$_2$, and X is CH$_2$, OCH$_2$ or CH$_2$O.

In principle, however, oxazolidinones in which the mesogenic group (R$^1$(—A$^1$)(—M$^1$)$_k$(—A$^2$)$_l$(—M$^2$)$_m$(—A$^3$)$_n$—) is in the 5-position on the oxazolidine ring are also subject-matter of the invention.

The oxazolidinones of the formula (I) or (II) can be obtained by multistep syntheses using individual reactions which are known from the literature. Further details on the general preparation methods are given in the experimental parts.

Said oxazolidinones are suitable as components for liquid-crystal mixtures. The LC mixtures preferably contain from 0.01 to 60% by weight, in particular from 0.1 to 20% by weight, particularly preferably from 0.1 to 5% by weight, of oxazolidinones. The other constituents are preferably selected from known compounds having nematic, cholesteric and/or smectic phases; these include, for example, Schiff's bases, biphenyls, terphenyls, phenylcyclohexanes, cyclohexylbiphenyls, N—, S—and O—containing heterocycles, for example pyrimidines, cinnamic acid esters, cholesterol esters and various bridged, polycyclic esters of p-alkylbenzoic acids with terminal polar groups. In general, commercially available liquid-crystal mixtures, even before the addition of the optically active compound(s), are mixtures of various components, of which at least one is mesogenic, i.e. a compound which, in derivatized form or mixed with other components, has a liquid-crystal phase which gives rise to expectations of the formation of at least one enantiotropic (clearing point > melting point) or monotropic (clearing point < melting point) mesophase.

The high twist capacity of the compounds according to the invention results, even in nematic phases in display technologies which are rather "classical", in advantageous possible uses. However, it is frequently not the compensation, but rather the achievement of twist through addition of the smallest possible amount of chiral dope that is in the spotlight. This applies both to TN ("twisted nematic") technology [see M. Schadt et al., Appl. Phys. Lett. 18, 127 (1971)] and to the so-called White-Taylor display [D. L. White et al., J. Appl. Phys. 45, 4718 (1974)] or the SBE/STN ("super birefringence effect"/"super twisted nematic") display [T. J. Scheffer et al., Appl. Phys. Lett. 45, 1021 (1984)] and its various modifications, such as the OMI ("optical mode interference") display [M. Schadt et al., Appl. Phys. Lett. 50, 236 (1987)].

The compounds according to the invention also induce a helix in the S$_c$ phase, which means that this effect can be utilized to compensate twist in the S$_c$* phase or to adjust it to a certain value, which is advantageous for use in practice [for example T. Tsuchiga et al., Jpn. J. Appl. Phys. 25, L-27 (1986)].

The liquid-crystal mixtures can be employed, for example, in electrooptical switching and display devices, which in addition contain, inter alia, the following components: two electrodes, two outer plates and at least one alignment layer. The structure of FLC displays is described in general terms in EP-B 0 032 362.

The invention is described in greater detail by means of the examples below.

EXAMPLES

General Synthetic Route for the Oxazolidinones of the Formula (I)

The oxazolidinone system is built up in a multistep synthesis starting from a (preferably natural) (chiral) amino acid or an amino alcohol. The coupling of the mesogenic group can take place in one reaction step or by stepwise build-up of the mesogen on the oxazolidinone.

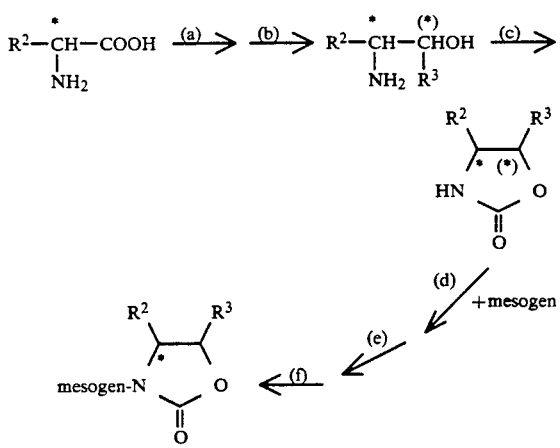

a) Reduction (for example lithium aluminum hydride)
b) Introduction of the "R$^3$" radical, for example oxidation using PCC (pyridinium chlorochromate) and then Grignard reaction
c) Cyclization using phosgene synthon
d, e and f) Coupling or stepwise build-up of the mesogenic side chain (R$^1$(—A$^1$)$_l$(—M$^1$)$_k$(—A$^2$)$_l$(—M$^2$)$_m$(—A$^3$)$_n$—X—).

The synthesis and coupling of a biphenyl mesogen to the oxazolidinone is described below schematically as an example:

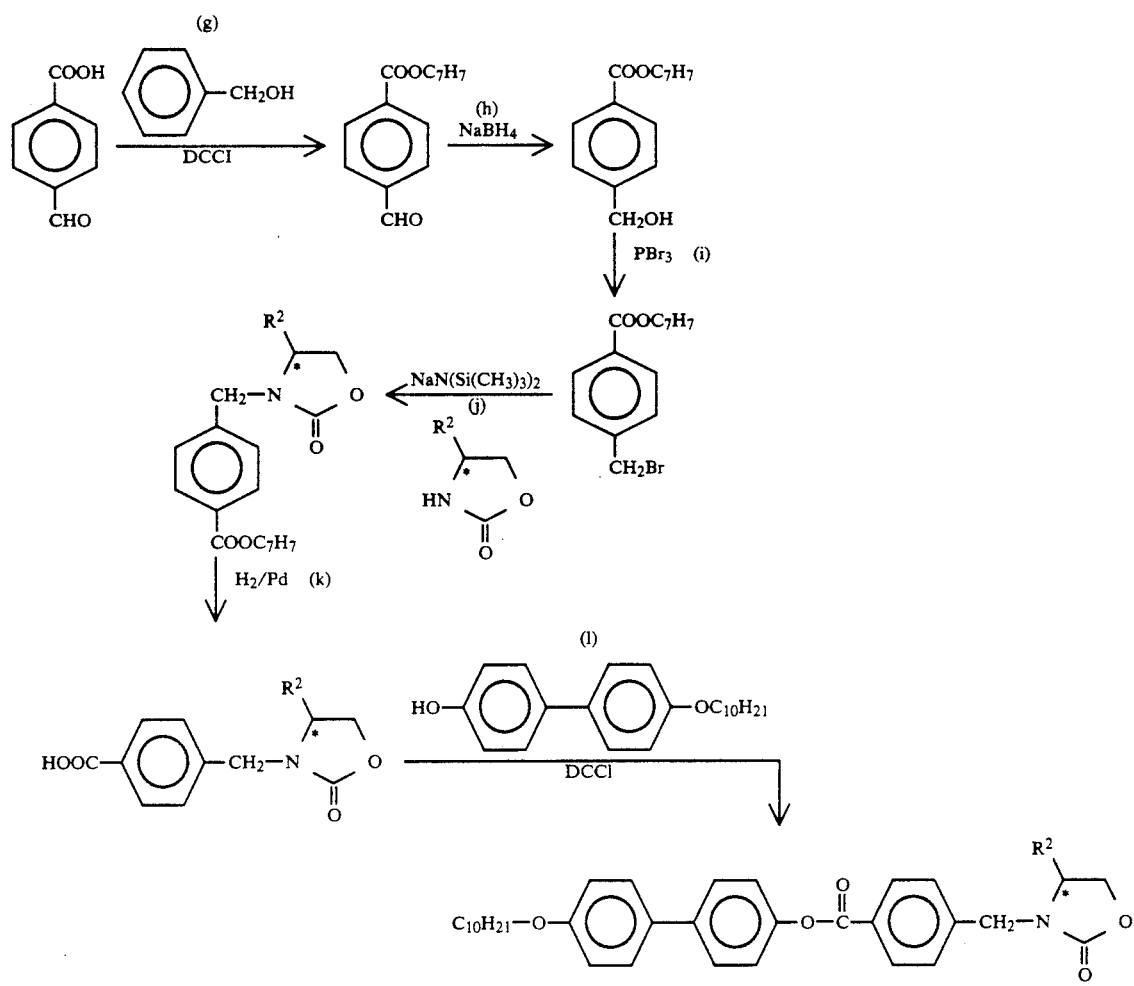

g) Esterification, for example using dicyclohexylcarbodiimide (DCCI)
h) Reduction using, for example, sodium borohydride
i) Conversion into the bromide using PBr₃
j) Fusing with the oxazolidinone ring
k) Hydrogenation of the ester, for example using Pd/charcoal
l) see g).

The oxazolidinones of the formula (II) can be synthesized, for example, in accordance with the following scheme:

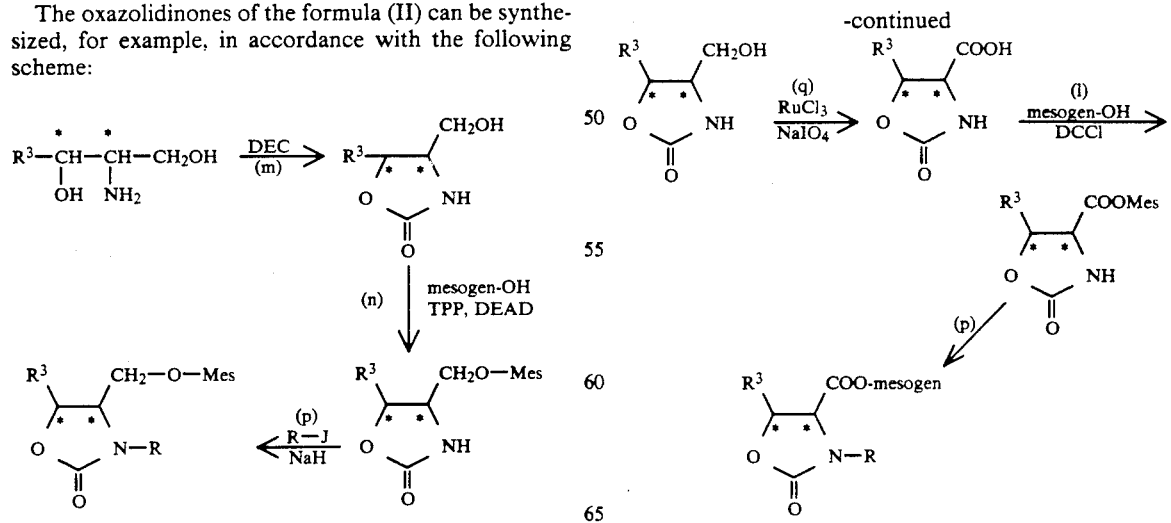

m) Condensation by means of, for example, diethyl carbonate (DEC)
n) Etherification using mesogenic alcohol, for example using triphenylphosphine (TPP), diethyl azodicarboxylate (DEAD)
p) N-Alkylation using, for example, alkyl iodide/sodium hydride
q) Oxidation, for example using sodium periodate/ruthenium(III) chloride trihydrate The example compounds below were prepared in accordance with the schemes sketched above using individual reactions which are known from the literature.

Synthesis of the Starting Materials

A. (2R)-(−)-2-Amino-2-phenylethanol 10 g (66 mmol) of D-phenylglycine are added in portions to a suspension of 3.66 g (96 mmol) of lithium aluminum hydride (LAH) in 130 ml of absolute THF. Conventional work-up and distillation (bath temperature: 90° C. at 0.8 mmHg) give a colorless, viscous liquid.

Yield: 7.7 g (56 mmol)=85%
$[\alpha]_D^{24} = -50.0°$ ()c=3.22, CHCl$_3$)
Empirical formula: C$_8$H$_{11}$NO (M=137.2)

B. (4R)-(−)-4-Phenyl-2-oxazolidinone 7.54 g (55 mmol) of (2R)-(−)-2-amino-2-phenylethanol are dissolved in 8 ml (61 mmol) of diethyl carbonate, 770 mg (5.5 mmol) of K$_2$CO$_3$ are added, and ethanol is removed by distillation via a column. The crude product is recrystallized from ether/petroleum ether.

Yield: 6.2 g (38 mmol)=69% (colorless crystals) m.p.=129° C.

C. (4R)-(−)-3-(4-Benzyloxycarbonylphenylmethyl)-4-phenyl-2-oxazolidinone 490 mg (3 mmol) of (4R)-(−)-4-phenyl-2-oxazolidinone are dissolved in 9 ml of absolute THF, first 3.3 ml of sodium bistrimethylsilylamide (1M in THF) and then 1050 mg (3.45 mmol) of benzyl 4-bromomethylbenzoate, dissolved in 2 ml of absolute THF, are added. The crude product is purified by chromatography (eluent: CH$_2$Cl$_2$)

Yield: 770 mg (2 mmol)=66% (colorless oil)
$[\alpha]_D^{23} = -85.9°$ (c=1.70)

D. (4R)-(−)-3-(4-Carboxyphenylmethyl)-4-phenyl-2-oxazolidinone 710 mg (1.8 mmol) of (4R)-(−)-3-(4-benzyloxy-carbonylphenylmethyl)-4-phenyl-2-oxazolidinone are dissolved in 18 ml of absolute ethanol, 70 mg of 10% Pd/C are added, and the mixture is hydrogenated.

Yield: 540 mg (1.8 mmol) =99%
$[\alpha]_D^{24} = -102.5°$ (c=2.85; CHCl$_3$)
IR: 3200–2300 (COOH); 1750, 1700 (C=O); 1615 (C=C); 1410; 1110

E. (2S)-(+)-2-Amino-1-propanol 8.9 g (100 mmol) of L-alanine are introduced in portions into a suspension of 5.55 g (146 mmol) of lithium aluminum hydride in 200 ml of absolute THF. Conventional work-up and distillation (bath temperature: 70° C. at 4 mmHg) give a colorless oil.

Yield: 3.37 g (45 mmol)=45% $[\alpha]_D^{23} = +19.6°$ (c=1.20; MeOH)
Empirical formula: C$_3$H$_9$NO (M=75.1)

F. (4S)-(+)-4-Methyl-2-oxazolidinone 3.2 g (42.5 mmol) of 2S)-(+)-2-amino-1-propanol are dissolved in 5.6 g (47 mmol) of diethyl carbonate, 600 mg (4.3 mmol) of K$_2$CO$_3$ are added, and the EtOH is removed by distillation via a column. Distillation (bath temperature: 160° C. at 0.1 mmHg) gives colorless crystals.

Yield: 2.60 g (25.5 mmol) =60%, m.p.: 66° C.
$[\alpha]_D^{23} = +7.8°$ (c=3.63; CHCl$_3$)
IR: 3460, 3270 (NH); 1755 (C=O); 1460; 1040; 945

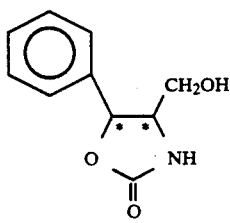

(I)

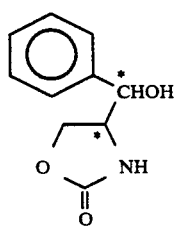

(II)

8.35 g (50 mmol) of 1-amino-3-phenyl-1,3-propanediol, 7.2 ml (55 mmol) of diethyl carbonate and 700 mg (5 mmol) of K$_2$CO$_3$ are introduced into a 50 ml flask. A Vigreux column with distillation bridge is attached. The suspension is heated at 130° C. for about 4 hours until 2 equivalents of ethanol have distilled off. The cooled mixture is taken up in methanol, and the K$_2$CO$_3$ is filtered off via Cellite. After evaporation, the crude product is purified by chromatography (silica gel/ether/methanol). According to NMR, the compounds (I) and (II) are in the ratio 9:1 in the crystalline product. Further separation is not necessary since only (I) is reacted in the subsequent reactions.

Yield of I+II: 9.26 g=96%, melting point 55° C.

H. Oxidation of G. to the Acid

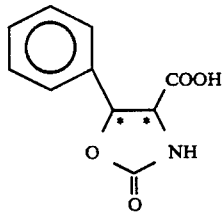

In the stated sequence 17.5 ml of tetrachloromethane, 17.5 ml of CH$_3$CN, 27.3 ml of H$_2$O, 2.0 g (10.5 mmol) of (I), 6.7 g (31.5 mmol) of NaIO$_4$ and 108 mg of RuCl$_3$.3-H$_2$O are combined and stirred overnight at 20° C. The batch is evaporated, and the residue is taken up in 70 ml of saturated NaCl solution and 70 ml of CH$_2$Cl$_2$. The phases are separated, the aqueous phase is extracted twice with CH$_2$Cl$_2$, the extracts are dried over MgSO$_4$, and the solvent is removed in vacuo. The crude product is purified by column chromatography (CH$_2$Cl$_2$/Et$_2$O).

Yield: 650 mg (45%)

EXAMPLE 1

(4S)-3-[4-(4,-Decyloxybiphenyl-4-oxycarbonyl)benzyl]-4-isopropyl-2-oxazolidinone

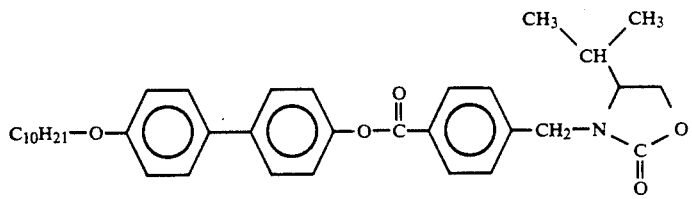

Melting point: 148° C.
$[\alpha]_D^{23}$: −6.9° (c=1.45, CHCl₃)

EXAMPLE 2

(4R)-3-[4-(4'-Decyloxybiphenyl-4-oxycarbonyl)benzyl]-4-phenyl-2-oxazolidinone

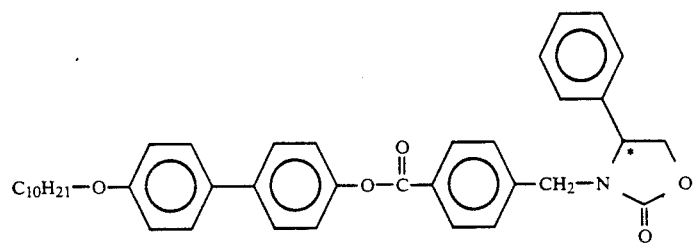

Melting point: 158° C.
$[\alpha]_D^{23}$: −90.2° (c=3.6, CHCl₃)

505 mg (1.07 mmol) of (4R)-(−)-3-(4-carboxyphenylmethyl)-4-phenyl-2-oxazolidinone and 555 mg (1.7 mmol) of 4-decyloxy-4'-hydroxybiphenyl and 31 mg of DMAP are dissolved in 17 ml of absolute CH₂Cl₂, and 390 mg (1.7 mmol) of DCCI are added. The crude product is purified by chromatography.

Yield 800 mg (1.3 mmol)=78% (colorless solid)
IR: 2930, 2860 (CH); 1740 (C=0); 1610, 1500 (C=C); 1410; 1270; 1080

EXAMPLE 3

(4S)-3-[4-(4,-Decyloxybiphenyl-4-oxycarbonyl)benzyl]-4-methyl-2-oxazolidinone

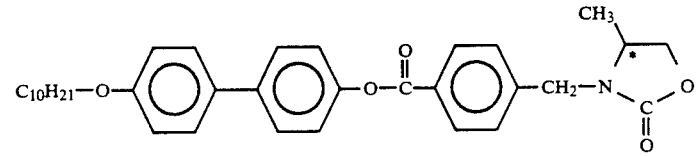

Melting point : 122° C.
Phase sequence: X 122 Sc* 134 I
$[\alpha]_D^{23}$: −15.5° (c=1.55, CHCl₃)

EXAMPLE 4

(5S)-3-[4-(4'-Decyloxybiphenyl-4-oxycarbonyl)benzyl]-5-methyl-2-oxazolidinone

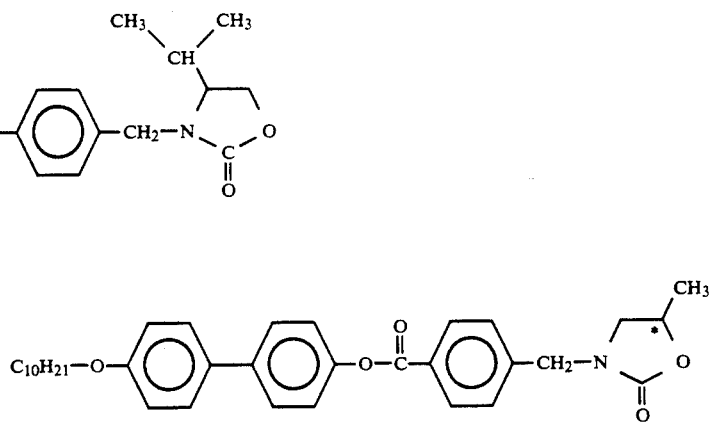

Melting point : 183° C.
$[\alpha]_D^{23}$: −14.7° (c=1.7, CHCl₃)

EXAMPLE 5

(4S,5S)-4-[4-(2-Octylpyrimidin-5-yl)phenyloxymethyl]--methyl-5-phenyl-2-oxazolidinone

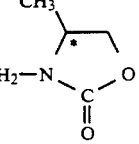

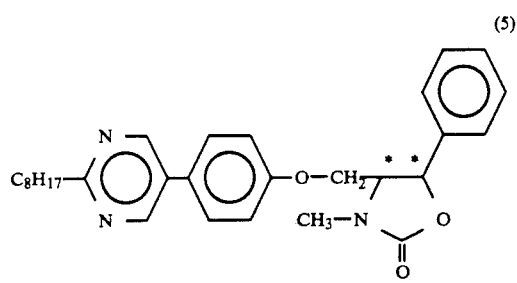

Melting point : 114° C.
¹H-NMR: δ=0.87 (t, 3H); 1.21–1.40 (m, 12H); 1.64 (2H); 2.60 (t, 7.5, 2H); 3.00 (S, 3H); 3.92 (t, 1H); 4.23 (dd, 1H); 4.26 (dd, 1H); 5.36 (d, 1H); 7.02–8.39 (9H, 4H); 7.35–7.45 (m, 5H); 8.58 (s, 2H)

EXAMPLE 6

4-[4-(2-Decylpyrimidin-5-yl)phenyloxymethyl]-5-phenyl-2-oxazolidinone

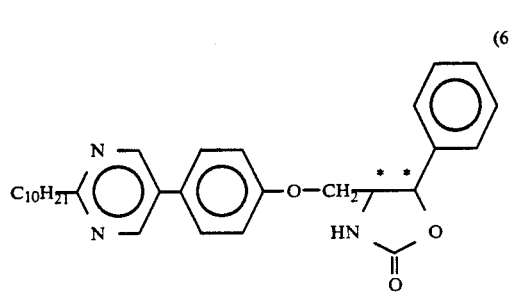
(6)

Melting point: 131° C.
¹H-NMR: δ=0.87 8 (t, 3H); 1.20–1.40 (m, 16Hz); 1.64 (q, 7.5Hz, 2H); 2.60 (t, 7.5Hz); 4.13–4.11 (m, 3H); 5.42 (dd, 1H); 5.80–5.87 (m, 1H); 6.98; 8.37 (8.5Hz); 7.37–7.47 (m, 5H); 8.59 (S, 2H)

538 mg (3 mmol) of oxazolidinylmethyl alcohol, 786 mg (3 mmol) of triphenylphosphine and 984 mg (3 mmol) of the pyrimidine derivative are dissolved in 50 ml of absolute THF in a flask, and 525 mg (3 mmol) of DEAD are added. The solution is stirred at 20° C. for 1 day. The THF is stripped off, and the crude product is purified twice by column chromatography (silica gel/methylene chloride/ether).

Yield: 750 mg (50%), melting point 131° C.

EXAMPLE 7

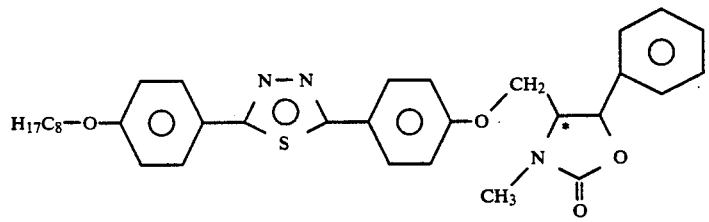

Melting point: 158° C.
¹H-NMR: δ=0.89 (t, 7Hz, 3H); 1.25–1.41 (m, 8H); 1.47 (quint); 1.81 (quint, 7Hz, 2H); 3.00 (S, 3H); 3.93 (dt, 1H); 4.02 (t, 7Hz, 2H); 4.22 (dd, 1H); 4.27 (dd, 1H); 5.36 (d, 6Hz, 1H); 6.98/7.92 (8.5Hz, 4H); 7.03/7.96 (8.5Hz, 4H); 7.37–7.46 (m, 5H)

EXAMPLE 8

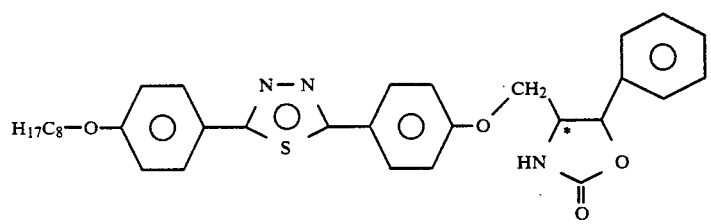

Melting point: 203° C.
¹H-NMR δ=0.88 (t, 7Hz, 3H); 1.23–1.39 (m, 8H); 1.47 (quint, 7Hz); 1.81 (quint, 7Hz, 2H); 4.02 (t, 7Hz, 2H); 4.13 (td, 1H); 4.17 (dd, 1H); 4.20 (dd, 1H); 5.36 (d, 5Hz, 1H); 6.89/7.78 (9Hz, 4H); 6.94/7.92 (9Hz, 4H); 7.37–7.46 (m, 5H)

EXAMPLE 9

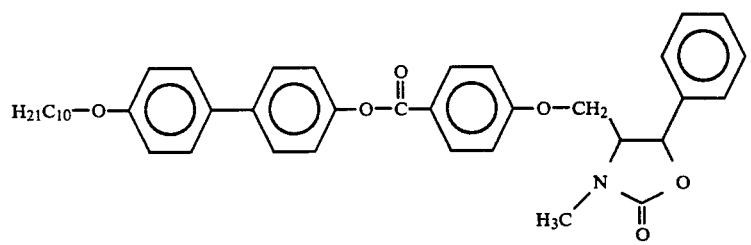

Melting point: 143° C.
¹H-NMR δ=0.89 (t, 7Hz, 3H); 1.24–1.42 (m, 12H); 1.47 (quintbr, 7Hz, ZM); 1.81 (quint, 7Hz, 2H); 3.01 (S, 3H); 3.94 (t, 6 and 4.5HZ, 1H); 4.00 (t, 7Hz, 2H); 4.25 (dd, 10 and 4.5Hz, 1H); 4.29 (dd, 10 and 4.5Hz, 1H); 5.37 (d, 6Hz, 1H); 6.97/7.51 (AA'BB', 8.5Hz, 4H); 7.04/8.21 (AA'BB', 8.5Hz, 4H); 7.37–7.47 (m, 5H)

EXAMPLE 10

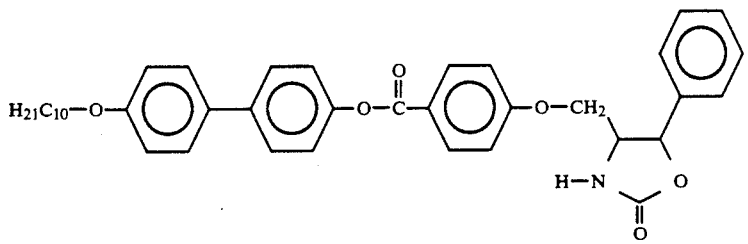

Melting point: 190° C.

$^1$H-NMR δ=0.89 (t, 7Hz, 3H); 1.19–1.35 (m, 12H); 1.46 (quintbr, 7Hz, 2H); 1.79 (quint, 7Hz, 2H); 4.03 (t, 7Hz, 2H); 4.36 (td, 5.5 and 5Hz); 4.43 (dd, 9.5 and 5.5Hz, 1H); 4.46 (dd, 9.5 and 5.5Hz, 1H); 5.73 (d, 5Hz, 1H); 7.21/7.70 (AA'BB', 9Hz, 4H); 7.21/8.33 (AA', BB', 9Hz); 7.51/7.78 (AA', BB', 9Hz, 4H); 7.60–7.68 (m, 5H)

USE EXAMPLES

Measurement Methods

The spontaneous polarization (Ps) is measured in a 10 μm cell by the method of Diamant et al. (Rev. Sci. Instr., 28, 30, 1957). At a layer thickness in the cell of about 2 μm, a uniform plane alignment of the liquid crystals in the $S_c^*$ phase is achieved by alignment layers [see SSFLC Technology, Clark et al., Appl. Phys. Lett. 36, 899 (1980)]. In order to determine τ and θ, the measurement cell is clamped on the rotary stage of a polarizing microscope between crossed analyzer and polarizer. The switching angle (2θ) is measured in a static electrical field applied over the measurement cell. For positive and negative polarity of this field, the measurement cell is in each case rotated until minimum light transmission occurs. The difference in angles between the two orientations determined in this way gives the switching angle. A photodiode is used to determine the response time (τ) by measuring the time taken for the light signal to increase from a signal level of 10 to 90%. The switching voltage is ±10 V/μm. In addition to the values for $P_s$, τ and 2θ, the $S^*$ range of the respective mixture is given; the values in parentheses indicate the super-coolable lower temperature limit of the $S_c$ range.

The pitch (Z) and the twisting power (HTP) in the cholesteric phase are determined as described, for example, in P. Kassubek et al., Mol. Cryst. Liq. Cryst., Vol. 8, 305–314, 1969, in a wedge cell with an alignment layer by measuring the dislocation lines under the polarizing microscope.

USE EXAMPLE A1 a) A liquid-crystalline mixture comprising 6 components

| | |
|---|---|
| 5-Octyloxy-2-(4-butyloxyphenyl)pyrimidine | 26.1 mol % |
| 5-Octyloxy-2-(4-hexyloxyphenyl)pyrimidine | 24.8 mol % |
| 5-Octyloxy-2-(4-octyloxyphenyl)pyrimidine | 11.4 mol % |
| 5-Octyloxy-2-(4-decyloxyphenyl)pyrimidine | 20.9 mol % |
| [4-(5-Decylpyrimidin-2-yl)]phenyl trans-4-pentylcyclohexanecarboxylate | 14.8 mol % |
| (5S)-3-[4-(4'-Decyloxybiphenyl-4-oxy-carbonyl]benzyl-5-methyl-2-oxazolidinone | 2 mol % | exhibits the following liquid-crystalline phase ranges:

$X 9 S_c^*$ 81.3 $S_A^*$ 91 $N^*$ 102.5 $I$

The HTP of the dope is shown in the table below.

| HTP | [μm$^{-1}$] | 1.45 | 1.96 |
|---|---|---|---|
| τ | [°C.] | 92 | 95 | b) By comparison, the liquid-crystalline mixture claimed in DE 3831226.3, which differs from the abovementioned mixture only in that it contains no dope, exhibits the following phase ranges:

$X 9$ $S_c 84$ $S_A 93$ $N$ 105 $I$

USE EXAMPLE A2 a) A liquid-crystalline mixture comprising 6 components

| | |
|---|---|
| 5-Octyloxy-2-(4-butyloxyphenyl)pyrimidine | 26.1 mol % |
| 5-Octyloxy-2-(4-hexyloxyphenyl)pyrimidine | 24.8 mol % |
| 5-Octyloxy-2-(4-octyloxyphenyl)pyrimidine | 11.4 mol % |
| 5-Octyloxy-2-(4-decyloxyphenyl)pyrimidine | 20.9 mol % |
| [4-(5-Decylpyrimidin-2-yl)]phenyl trans-4-pentylcyclohexanecarboxylate | 14.8 mol % |
| (4R)-3-[4-(4'-Decyloxybiphenyl-4-oxy-carbonyl]benzyl-4-phenyl-2-oxazolidinone | 2 mol % | exhibits the following liquid-crystalline phase ranges:

$X 9$ $S_c^*$ 76 $S^*$ 89 $N^*$ 101 $I$

The HTP of the dope is shown in the table below.

| HTP | [μm$^{-1}$] | 12.1 | 13.5 | 14.5 | 15.7 | 17.2 |
|---|---|---|---|---|---|---|
| τ | [°C.] | 89 | 91 | 93 | 95 | 97 |

By contrast, other mixtures, which differ from the abovementioned mixture in that they contain different dopes (likewise in an amount of 2 mol-% in the total mixture), have the twisting power mentioned below in Table 1:

TABLE 1

The HTP values of comparative mixtures of different dopes in the base mixture of Example A1 were determined at a temperature of 95° C.:

| Comparative example | Structure | | HTP [μm$^{-1}$] |
|---|---|---|---|
| 2b | C$_8$H$_{17}$—O—⟨phenyl⟩—C(=O)—O—⟨phenyl⟩—⟨phenyl⟩—O—C(=O)—*C—(tetrahydrofuran) | (R) | +0.1 |
| 2c | C$_{10}$H$_{21}$—O—⟨phenyl⟩—C(=O)—O—⟨phenyl⟩—O—C(=O)—*C—(tetrahydrofuran) | (R) | +1.1 |
| 2d | C$_8$H$_{17}$—O—⟨pyrimidine⟩—⟨phenyl⟩—O—C(=O)—*C—(tetrahydrofuran) | (R) | +2 |
| 2e | C$_8$H$_{17}$—⟨pyrimidine⟩—⟨phenyl⟩—O—CH$_2$—**(epoxide)—C$_4$H$_9$ | (2S, 3S) | −1.5 |
| 2f | C$_2$H$_5$—*CH(CH$_3$)—(CH$_2$)$_6$—O—⟨pyrimidine⟩—⟨phenyl⟩—O—C(=O)—*CHCl—CH(CH$_3$)$_2$ | (2S, 3S) | −0.15 |
| 2g | C$_9$H$_{19}$—O—⟨phenyl⟩—⟨phenyl⟩—O—C(=O)—*CHF—CH(CH$_3$)$_2$ | (S) | −1.7 |
| 2h | C$_8$H$_{17}$—O—⟨pyrimidine⟩—⟨phenyl⟩—O—C(=O)—*C—(dioxolane with gem-dimethyl) | (R) | −0.7 |

It can be seen from Table 1 that the dope according to the invention has a surprisingly large HTP in the basic mixture from A1 and is therefore particularly suitable for compensation of the pitch of other dopes.

USE EXAMPLE A3 a) A liquid-crystalline mixture comprising 6 components

| | |
|---|---|
| 5-Octyloxy-2-(4-butyloxyphenyl)pyrimidine | 26.1 mol % |
| 5-Octyloxy-2-(4-hexyloxyphenyl)pyrimidine | 24.8 mol % |
| 5-Octyloxy-2-(4-octyloxyphenyl)pyrimidine | 11.4 mol % |
| 5-Octyloxy-2-(4-decyloxyphenyl)pyrimidine | 20.9 mol % |
| [4-(5-Decylpyrimidin-2-yl)]phenyl trans-4-pentylcyclohexanecarboxylate | 14.8 mol % |
| (4S)-3-[4-(4′-Decyloxybiphenyl-4-oxycarbonyl]benzyl-4-isopropyl-2-oxazolidinone | 2 mol % | exhibits the following liquid-crystalline phase ranges:

X9 S$_C$*79 S$_A$* 90 N* 102.5 I

The HTP of the dope is shown in the table below.

| HTP [μm$^{-1}$] | 5.7 | 6.2 | 6.6 | 7.3 |
|---|---|---|---|---|
| τ [°C.] | 90 | 93 | 96 | 99 |

This dope also has an HTP which is significantly higher than for the comparative dopes listed in Table 1. This dope is thus also very suitable for compensation of a pitch.

We claim:

1. A chiral oxazolidinone of the formula (I) or (II)

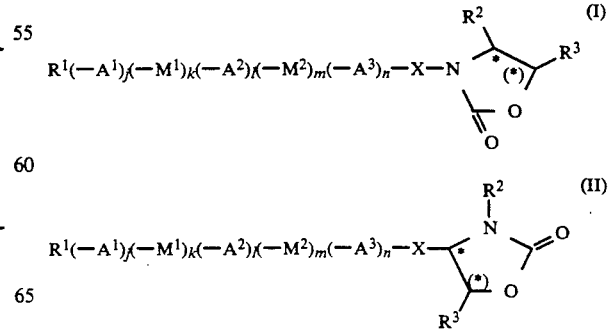

in which

\* is a chiral center, (\*) is an optional chiral center, $R^1$ is a straight-chain alkyl radical having 1 to 16 carbon atoms, it being possible for one —CH$_2$— groups to be replaced by —O—, —$R^2$ and —$R^3$, independently of one another, are —H, alkyl having 1 to 12 carbon atoms, or are -phenyl, j and l are zero, 1 or 2, k and m are zero or 1, and n is zero, 1 or 2, with the proviso that k is zero if j and/or l are zero; m is zero if n is zero; the sum of j+l+n is at least 1 and at most 3, —$A^1$ and —$A^2$ are

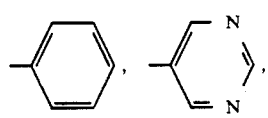

—$A^3$ is

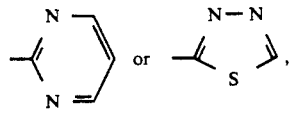

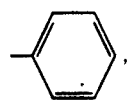

—$M^1$ and —$M^2$ are —CO—O or —O—CO, and

—X— is —O—CH$_2$ or —CH$_2$—.

2. A liquid-crystal mixture comprising at least two components and containing at least one chiral oxazolidinone as claimed in claim 1.

3. A ferroelectric liquid-crystal mixture comprising at least two components and contains, as dope, an oxazolidinone as claimed in claim 1.

4. A ferroelectric liquid-crystal mixture comprising two components and containing from 0.1 to 20% by weight of an oxazolidinone as claimed in claim 1.

5. A smetic liquid-crystal mixture comprising at least two compounds and having at least one chiral oxazolidinone as claimed in claim 1.

\* \* \* \* \*